United States Patent
Shea

(10) Patent No.: US 8,002,410 B2
(45) Date of Patent: Aug. 23, 2011

(54) USER-PROPOSED ENTRY FIELD(S) FOR CUSTOMIZED DATA ANALYSIS/PRESENTATION

(75) Inventor: William Shea, Pleasanton, CA (US)

(73) Assignee: Clarity Medical Systems, Inc., Pleasanton, CA (US)

( * ) Notice: Subject to any disclaimer, the term of this patent is extended or adjusted under 35 U.S.C. 154(b) by 0 days.

(21) Appl. No.: 12/643,945

(22) Filed: Dec. 21, 2009

(65) Prior Publication Data

US 2010/0165290 A1 Jul. 1, 2010

Related U.S. Application Data

(63) Continuation-in-part of application No. 12/605,219, filed on Oct. 23, 2009.

(51) Int. Cl.
*A61B 3/10* (2006.01)

(52) U.S. Cl. .................... 351/205; 351/211

(58) Field of Classification Search ........... 351/200–246
See application file for complete search history.

(56) References Cited

U.S. PATENT DOCUMENTS

| | | | |
|---|---|---|---|
| 4,141,652 A | 2/1979 | Feinleib | |
| 5,164,578 A * | 11/1992 | Witthoft et al. ............ | 250/201.9 |
| 5,568,208 A | 10/1996 | Van de Velde | |
| 5,777,719 A | 7/1998 | Williams | |
| 6,199,986 B1 | 3/2001 | Williams et al. | |
| 6,376,819 B1 | 4/2002 | Neal | |
| 6,685,317 B2 | 2/2004 | Su | |
| 6,709,108 B2 * | 3/2004 | Levine et al. ............ | 351/211 |
| 6,791,696 B1 | 9/2004 | Fantone | |
| 6,827,444 B2 * | 12/2004 | Williams et al. ............ | 351/212 |
| 6,964,480 B2 | 11/2005 | Levine | |
| 7,665,846 B2 * | 2/2010 | Campin et al. ............ | 351/208 |
| 7,771,048 B2 * | 8/2010 | Dai et al. ............ | 351/205 |
| 2002/0169441 A1 | 11/2002 | Lemberg | |
| 2003/0053031 A1 | 3/2003 | Wirth | |
| 2004/0004696 A1 | 1/2004 | Davis et al. | |
| 2004/0156015 A1 | 8/2004 | Campbell | |
| 2005/0134851 A1 | 6/2005 | Murphy | |

OTHER PUBLICATIONS

Dave, T., "Wavefront aberrometry Part 1: Current Theories and Concepts", Optometry Today, Nov. 19, 2004, pp. 41-45.
Ginis, H.S. et al., Variability of wavefront aberration measurements in small pupil sizes using a clinical Shack-Hartmann aberrometer, BMC Ophthalmology, Feb. 11, 2004, 4:1 copyright 2004 Ginis et al.
Liang, J. et al., Objective measurements of wave aberrations of the human eye with the use of a Hart-Shackman wave-front sensor, J. Opt. Soc. Am. A., vol. 11, No. 7, Jul. 1994, pp. 1949-1957, copyright 1994 Optical Society of America.

* cited by examiner

*Primary Examiner* — Mohammed Hasan
(74) *Attorney, Agent, or Firm* — Charles E. Krueger

(57) ABSTRACT

One embodiment of the present invention is a method to not limit the device's manipulation of the data to that of the manufacturer, but to allow greater freedom for customization by the individual user for their preference.

14 Claims, 6 Drawing Sheets u = measured spherical refractive error of an aphakic eye v = measured cylindrical refractive error of an aphakic eye w=0.07 $(u+0.5v)^2$ + 1.27 (u + 0.5v) + 1.22

USER-PROPOSED ENTRY FIELD(S) FOR CUSTOMIZED DATA ANALYSIS/PRESENTATION

RELATED APPLICATIONS

This application is a continuation-in-part of application Ser. No. 12/605,219 entitled Optimizing Vision Correction Procedures, filed Oct. 23, 2009 which is a continuation of application Ser. No. 11/761,890 entitled Adaptive Sequential Wavefront Sensor, filed Jun. 12, 2007, which is a continuation of application Ser. No. 11/335,980 entitled Sequential Wavefront Sensor, filed Jan. 20, 2006 now U.S. Pat. No. 7,445,335, issued Nov. 4, 2008, all of which are incorporated by reference for all purposes.

TECHNICAL FIELD

One or more embodiments of the present invention relate generally to data manipulation and presentation. In particular, the invention relates to user interface of a device which allows the individual user to customize the manipulation of data collected or captured by a device.

BACKGROUND OF THE INVENTION

Traditionally, measurement devices are provided to the end user with built-in control for data collection, processing and presentation or display. The end users thus do not have the freedom to manipulate the data to their preference. For some applications such as those in ophthalmology, there is sometimes a need to provide the end user the freedom to choose a preferred form, format, transfer function, application, expression, output, and/or an algorithm for data manipulation.

SUMMARY OF THE INVENTION

One or more embodiments of the present invention satisfy one or more of the above-identified need(s) in the art. In particular, one embodiment of the present invention is a method for allowing the end user to choose the way of customizing the manipulation of the data captured from a measurement device.

BRIEF DESCRIPTION OF THE DRAWINGS

FIGS. 3 and 4 depict screen shots of user output from an embodiment;

DETAILED DESCRIPTION OF EXAMPLE EMBODIMENTS

Reference will now be made in detail to various embodiments of the invention. Examples of these embodiments are illustrated in the accompanying drawings. While the invention will be described in conjunction with these embodiments, it will be understood that it is not intended to limit the invention to any embodiment. On the contrary, it is intended to cover alternatives, modifications, and equivalents as may be included within the spirit and scope of the invention as defined by the appended claims. In the following description, numerous specific details are set forth in order to provide a thorough understanding of the various embodiments. However, various embodiments may be practiced without some or all of these specific details. In other instances, well known process operations have not been described in detail in order not to unnecessarily obscure the present invention. Further, each appearance of the phrase an "example embodiment" at various places in the specification does not necessarily refer to the same example embodiment.

In accordance with one or more embodiments of the present invention, the end-user of a measurement device such as a wavefront sensor for eye refractive error or aberration is provided with freedom of manipulating the devices' resultant datum or data to a form, format, transfer function, application, expression, output, and or an algorithm that he/she so chooses.

Figure 1:
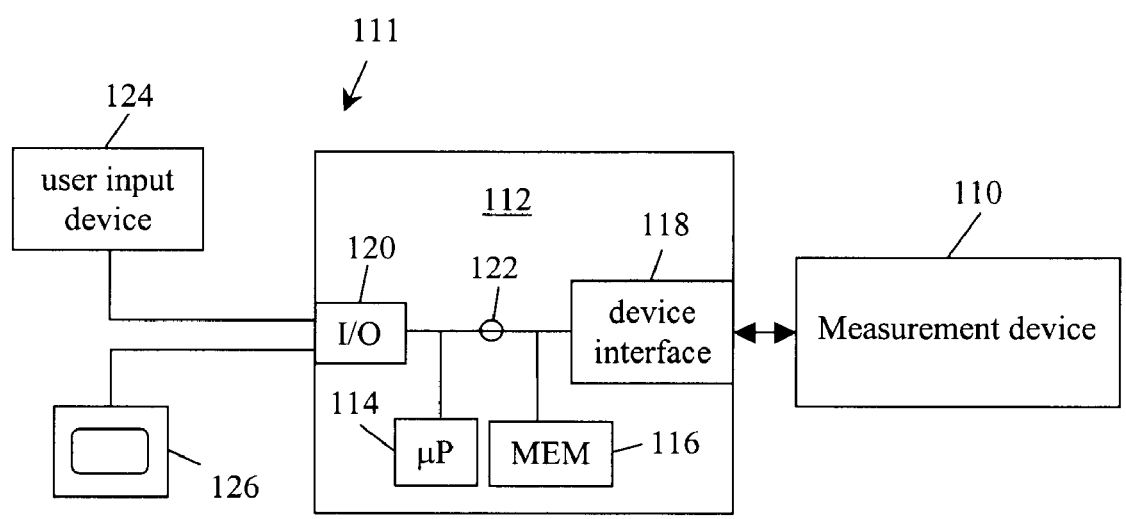
FIG. 1 depicts a block diagram of an example embodiment.

FIG. 1 is a block diagram of an example embodiment. Referring to FIG. 1, a measurement device 110 is coupled to a device interface 111 including controller 112 including a processor 114, a memory 116, a device interface 118, and I/O interface 120 and an internal bus 122 coupling the various components of the controller. A user-input device 124, such as a keyboard or mouse, and an output device 126, such as a display are coupled to the I/O interface 120.

The measurement device 110 is coupled to the device interface 118 (or alternatively to the I/O interface 120) and provides as raw data the results from a measurement to the controller 112.

The purpose is to not limit the device's manipulation of the data to that of the manufacturer, but to allow greater freedom for customization by the individual user for their preference, which can potentially change with different applications of the device. It solves the varying and unique needs of the end users to control what processes they want to be applied (specific algorithms, filters, and analyses, for example) to the data and to be displayed to meet their varying needs. These processes can be applied real time, saved off for later use, sent over the intranet or internet, for examples. They can occur simultaneously or discretely per the user's choice.

Figure 2:
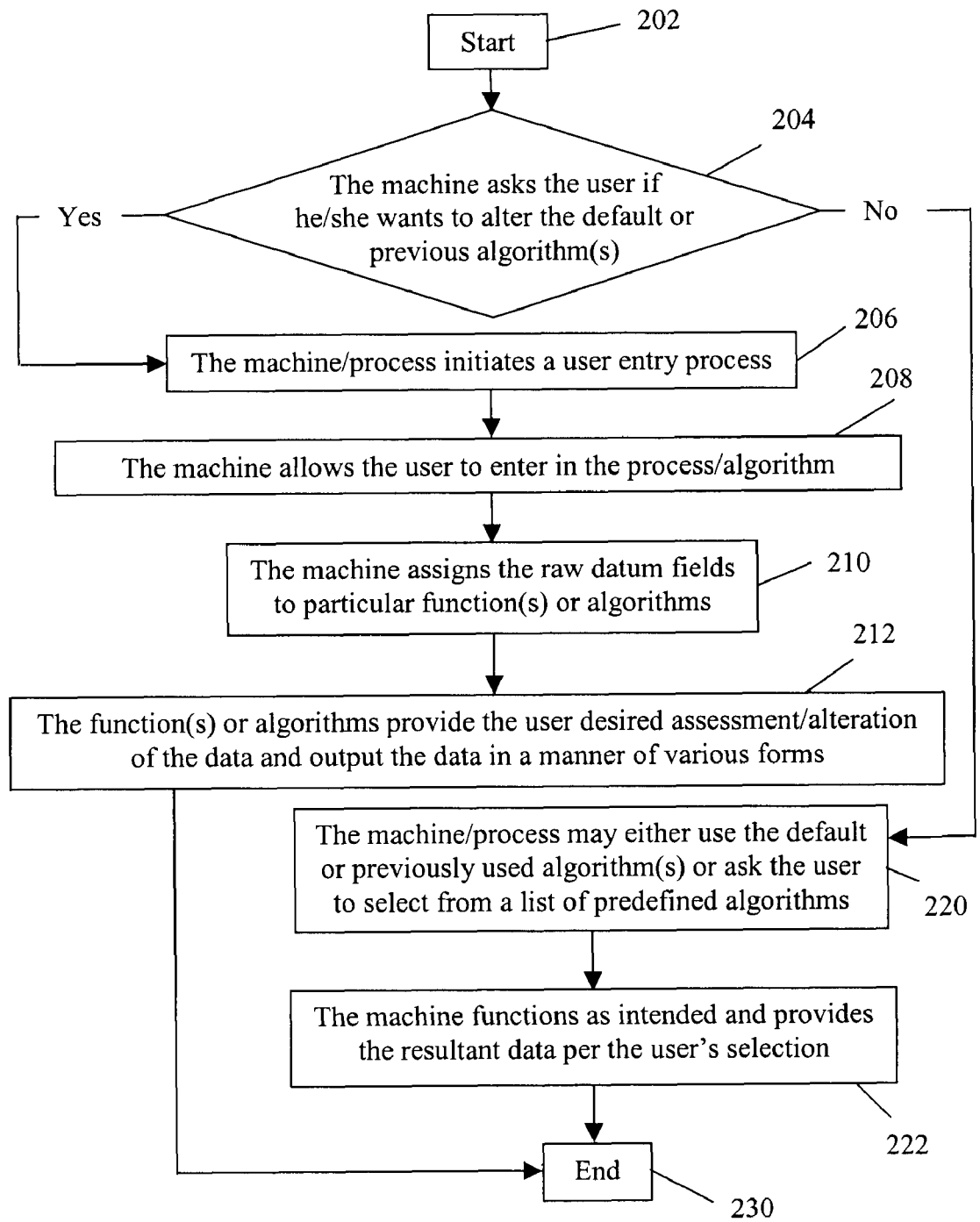
FIG. 2 shows a block diagram of the steps involved in one embodiment of presently disclosed method.

This is a new method and process(es) that can be applied to existing and future products. FIG. 2 shows an example flow diagram of the steps. In an example embodiment these steps would be implemented by the controller when executing a program stored in the memory. The raw data supplied by the measurement device would also be stored in the memory.

At the start step 202, the device's application/process would initiate or run.

At the next step 204, which can be part of the process initialization or invoked by the user, the "Machine" asks the user if they would like to alter the default or previous algorithm(s) used for displaying or representing or storing or transmitting resultant information from the collected or acquired data. In particular, the default or previous algorithm(s) can be that of a wavefront sensor for eye refractive error or aberration measurement(s).

If the user selects "No", the process moves to step 220 at which the machine may either use the default or previously used algorithm(s) or ask the user to select from a list of predefined algorithms.

Once the selection is made, the machine functions as intended, while providing the resultant data per the user's selection as shown by step 222, which is followed by the end step 230.

On the other hand, if the user selects "Yes", the machine initiates a user entry process as shown by step 206.

At step 208, the machine allows the user to enter in the process or algorithm.

In the next step 210, the machine assigns the raw datum fields to a particular function, functions, or algorithms.

In step 212, the function(s) or algorithms provide the user their desired assessment/alteration of the data and output it in a manner of various forms before the end step 230.

As an option, these algorithms could be entered real time, for example with a keyboard, or imported from another medium.

As another option, the machine could also provide the user a set of predetermined algorithms or processes that could be applied separately or in combination with the data from the machine. For example there could be a low-pass filter algorithm/module and a polar coordinate transfer function/module. The user could select to have the data converted to polar coordinates then low-pass filtered.

Any of the above inputs could be saved for future use. Thereby, allowing the user to create a "library" of custom/canned functions/applications.

As still another option, the user could also be prompted by the machine to determine the desired output method or methods for the above. For example, the user could opt for a graphical display, audio, or numeric, or all. The output data could also be exported to another application or machine/device to affect its functionality or not, or as a combination of data usage/storage.

The machine could present the predefined algorithms/applications such that the user could be prompted to change the currently applied algorithm/application to a new one real time, without the need to pause or stop the machine's current process(es).

Additionally, the user could be prompted to customize the manner in which the resultant data, raw or processed, is to be presented. The machine could prompt the user to select a graphical display, the type of display and the data limits displayed. Alternatively the user could select that the data be displayed, processed or raw, with or without a graphical component.

In general, the data/datum from a device that is provided either from or through a microprocessor, over a communication link, or displayed can be input into a user created and selected process or processes. The user would have the ability to direct specific data or datum into a specific input (independent variable) field of their creation(s).

For example, a device's processor could present data visually to the end user on an LCD (liquid crystal display). This data could be presented as a continuous set of data representing a line in the form, y=mx+b (manufacturer's default). The end user may want the data presented and fit as a third order polynomial, $y=k_3x^3+k_2x^2+k_1x+k_0$. The device's processor would provide a user interface mechanism/method allowing the user to enter in the equation, $y=k_3x^3+k_2x^2+k_ix+k_0$, and uniquely direct/assign the datum (independent variable) into their equation. The user could then select how he/she wants the results of the equation used; presented real time as a 'y' (dependent variable), graphed as the "fit" line, saved off for post review, transmitted elsewhere, or all the above.

For example, if the raw datum fields were the measured spherical refractive error and measured cylindrical refractive error of an aphakic eye given by an autorefractor, then these raw datum fields could be assigned to parameters labeled u and v, respectively. If the user requires a resultant value, w, assigned to the power of an intraocular lens (IOL) then the algorithm "w=0.07 $(u+0.5v)^2$+1.27 (u+0.5v)+1.22" can be entered using the user input device.

Functions other than polynomials, such as, for example, logarithm and exponential functions can also be provided for use in user-supplied algorithms.

Figure 4:
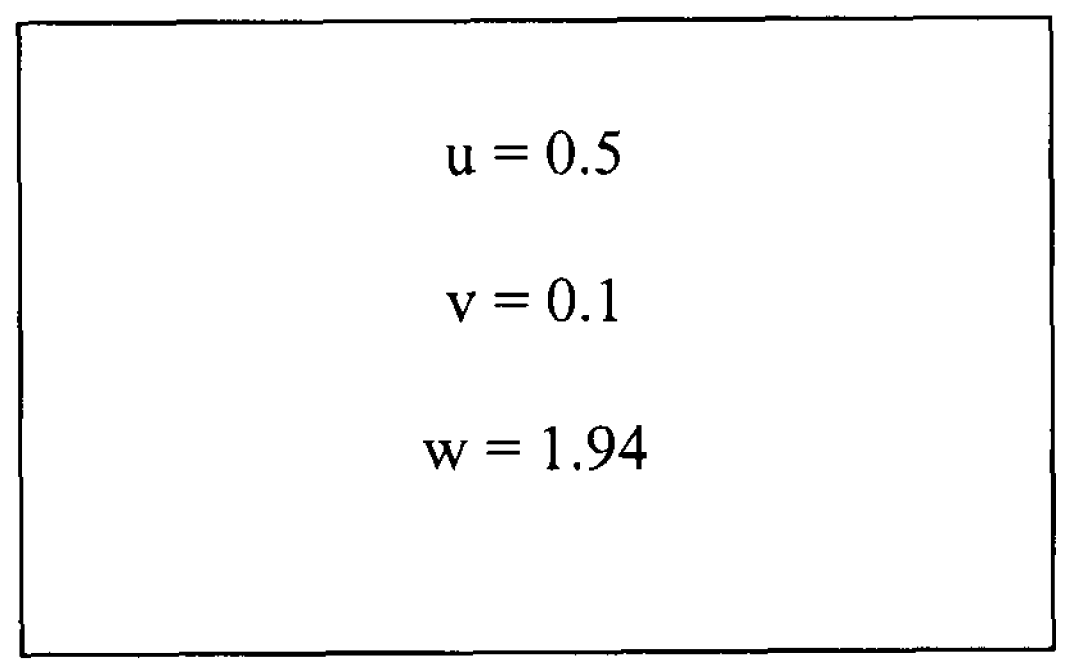

FIGS. 3 and 4 are example screen shots for the above describe process. In FIG. 3 the assignment of the raw data to variables is defined and the user is prompted to enter an algorithm. In FIG. 4 the data values assigned to the variables and resultant value are displayed.

The present method provides the user great flexibility to fully utilize the processors' and device's capability and to maximize the end product for their use.

This technique/approach can be applied to any device, processor, or method that contains, supplies, and/or creates data. Embodiments can be autorefractors or wavefront sensors where the device's data can be used for a multitude of outcomes/uses such as prescriptions, 3 or 2 dimensional graphs, averaged; ophthalmic cameras where the photographic data can be processed through a custom algorithm such as a FFT; a Pulse oximeter output where the beat-to-beat data could be processed for unique events.

The example embodiment can be implemented manually, orally, scripted, and/or provided in a separate application/process to the primary process. This process can occur prior to, during, or after the use of the machine/device. Thereby allowing the user the flexibility to plan the desired outcome(s) prior to initiating the use of the machine/device; adjust the outcomes real time during the use of the machine/device; or post use in assessing the collected data using a variation of processes. The scripting of the application can occur discretely a single fixed application or as a multitude of applications that could occur sequentially, randomly, or for a preferred application or utilization of the machine/device or process.

A more detailed description of an embodiment of a device interface integrated with a particular wavefront sensor designed by the assignee of the current application will now be described. In this embodiment the raw measurement data includes, for example, spherical refractive error, cylindrical refractive error, and high-order aberrations such as coma, trefoil, and spherical aberrations. The measurement device will now be described.

Figure 5:
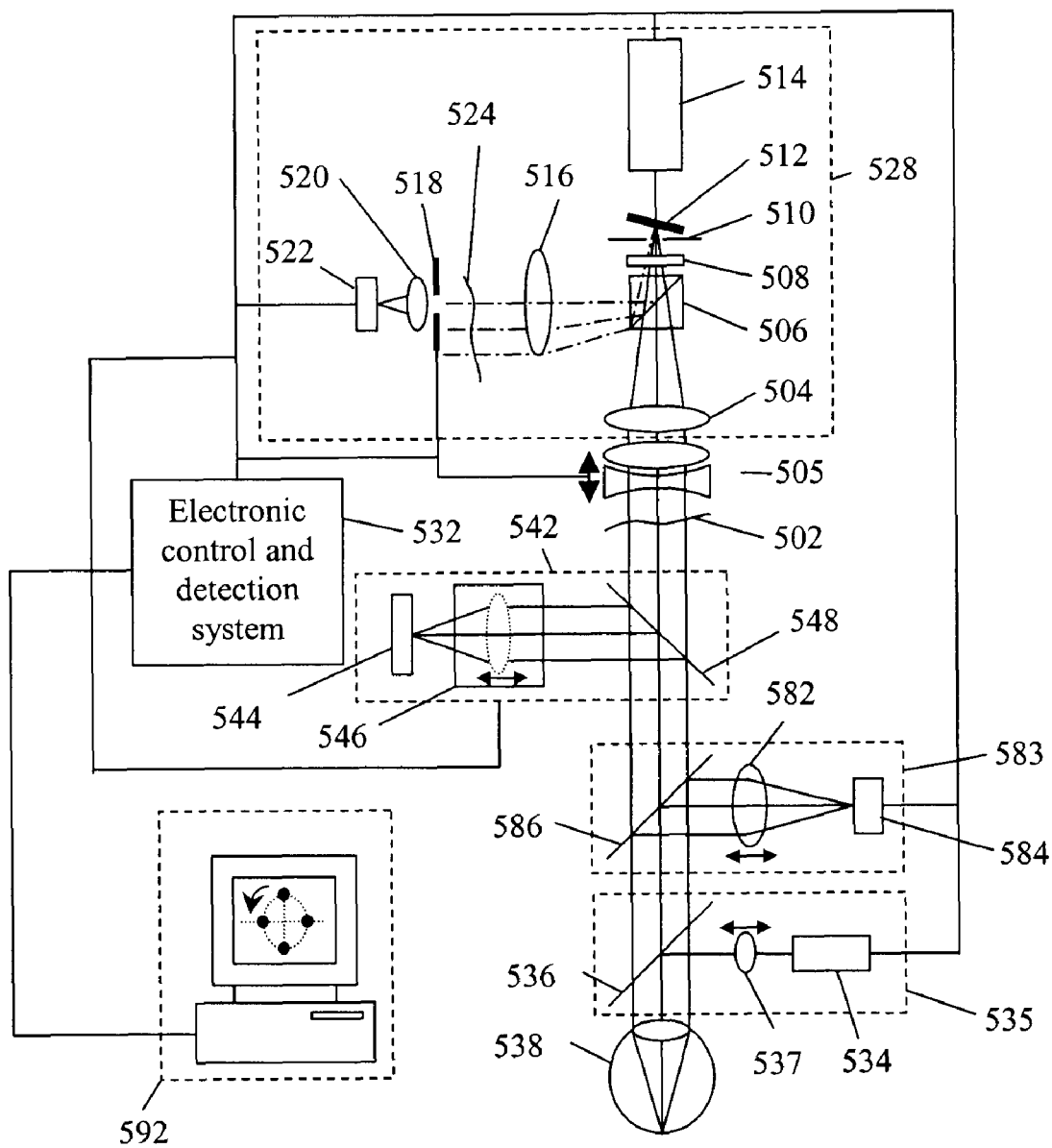
FIG. 5 shows a schematic diagram of one embodiment in which a dynamic defocus offsetting device is used to offset spherical refractive error of the wavefront from an eye.

FIG. 5 shows one embodiment of a dynamic wavefront sensing system in which a defocus offset device is used to offset the spherical refractive error component of the wavefront from an eye.

A sequential wavefront sensor 528 has a first lens 504 that focuses a linearly polarized input beam of light having a wavefront 502. The focusing beam travels through a polarization beam splitter (PBS) 506, which is arranged in such a manner that its pass-through polarization direction is aligned with the polarization direction of the incoming beam. As the result, the linearly polarized convergent beam will pass through the PBS 506. A quarter-wave plate 508 is placed behind the PBS 506 with fast axis oriented so that a circularly polarized beam is emerged after passing through the quarter-wave plate 508. A pinhole 510 is placed behind the quarter wave plate 508 and right in front of the scanning mirror 512 to serve the purpose of rejecting the light not directly coming from interested wavefront of the light beam.

The input convergent beam, after passing through the pinhole 510, is focused on the reflective surface of a tilted scanning mirror 512, which is mounted on the shaft of a motor 514. The light beam reflected by the mirror is divergent, with its beam central chief ray changed to a direction that is dependent on the tilting angle of the scan mirror 512 and the rotational position of the motor 514. It is expected that the reflected beam is still circularly polarized, but the circular polarization rotation direction will be changed from left hand to right hand or from right hand to left hand. Hence, upon passing through the quarter-wave plate 508 for a second time on its return path, the beam becomes linearly polarized again, but with its polarization direction rotated to an orthogonal direction with respect to that of the original incoming beam. Therefore, at the polarization beam splitter 506, the returned beam will be mostly reflected to the left as shown by the dashed light rays in FIG. 5.

A second lens 516 is placed on the left next to the PBS 506 to collimate the reflected divergent beam and to produce a replica of the original input wavefront. Due to the tilting of the scan mirror, the replicated wavefront is transversely shifted. An aperture 518 is placed behind the second lens 516 and right in front of the sub-wavefront focusing lens 520 to select a small portion of the replicated wavefront. The sub-wavefront focusing lens 520 focuses the selected sub-wavefront onto a position sensing device 522, which is used to determine the centroid of the focused light spot generated from the sequentially selected sub-wavefronts. By rotating the motor 514 and changing the tilting angle of the scan mirror 512 in a continuous or stepped fashion, the amount of radial and azimuthal shift of the replicated wavefront can be controlled such that any potion of the replicated wavefront can be selected to pass through the aperture 518 in a sequential way. As a result, the overall wavefront of the original incoming beam can be characterized as for the case of a standard Hartmann-Shack wave-front sensor with the exception that the centroid of each sub-wavefront is now obtained in a sequential rather than a parallel manner.

When the tilt angle of the scanning mirror remains constant an annular section of the wavefront 502 is sequentially scanned. The radius of the annular section can be changed by changing the tilt of the scanning mirror.

The light source module 535, comprising the light source 534, the collimating lens 537 and the beam directing element 536, is used to direct a narrow beam of light onto the retina of a patient eye 538. It has been mentioned in US20080278683 that the infrared imaging module 583 can be used to monitor the position of the fovea and also to align and register the eye. In addition, the internal fixation and visual acuity projection module 542 as shown in FIG. 5 can comprise a micro display 544, a variable focus lens 546 and a beam directing element 548, and serve the function of changing the accommodation of the patient's eye as well as checking the patient's visual acuity. When the patient's accommodative mechanism of the eye is not anaesthetized, a continuous measurement of wavefront aberrations over the full accommodation range will provide an optimized prescription for vision correction. In spite of the fact that these two modules are shown, it should also be understood that they are not absolutely required for the apparatus embodiment.

However, as one aspect of an embodiment, the internal fixation/visual acuity projection module can also be used to change the accommodation of the patient's eye with wavefront measurements also done for the whole accommodation range. During accommodation, while the axis of fixation may not change which means proper patient alignment, the actual visual axis or center may vary, indicating a kind of pseudo accommodation or non-symmetric visual correction. The wavefront sensor can record the variation and determine accommodative correction.

As another aspect of an embodiment, the internal fixation/visual acuity projection module can also be used to guide the patient to look off-axis so that the incident light beam can be guided to land on different positions of the retina rather than at the fovea region. This can be achieved by turning a certain pixel or group of pixels of the micro display 544 on and as a result, the eye will be directed to fixate on the "on" pixel(s), making it possible to capture the eye aberration wavefront for both the center and the peripheral light scattering locations. In doing so, wavefront aberrations can be measured as a function of the landing position of the incident light beam and therefore a 2D array of wavefront aberrations for light scattered from different locations on the retina can be generated. Such a 2D array of wavefront measurements will provide a vision correction practitioner with additional valuable information in addition to a conventional eye aberration wavefront measurement resulting from only a central light scattering location. This will further optimize aberration correction prescriptions in the sense that in addition to central vision, peripheral vision can also be optimized.

In FIG. 5, active defocus offsetting is achieved by changing the effective focal length or the spherical refractive power of a lens or a lens combination 505 disposed in the optical path in front of a wavefront sensor 528. The change of the effective focal length can be calibrated to indicate the correction in diopters (for example) required to change the actual wavefront returned from the retina to a plane wave. This correction in diopters is the refractive prescription for correcting the vision of a patient. The procedures for obtaining this prescription for spherical and astigmatic aberrations are described in detail below.

Note that the difference between the current embodiment and those disclosed in U.S. Pat. No. 7,445,335 and US20080278683 is that a dynamic defocus offsetting element 505 is arranged in the light path. Previous embodiments only mentioned the compensation or defocus nulling function if such an element is used. In the current embodiment, in addition to the compensation or nulling function, the defocus offsetting element 505 also provides active off-setting or partial cancellation of the spherical refractive error component in either the positive or negative direction to make the wavefront more or less spherically divergent or convergent and the active offset is at the disposal of the refractive surgeon or controlled by a built-in algorithm according to the real time display and/or feedback of the wavefront measurement.

One aspect of the embodiment is to use the defocus offset device to partially compensate for any relatively large spherical refractive error so that the remaining spherical and cylindrical refractive errors and other higher order aberrations all fall within the measurement dynamic range of the wavefront sensor. As such, the variable focal length lens is functioning as an optical component that can also substantially increase the measurement dynamic range of the combined wavefront sensing system. Another aspect of the embodiment is to scan the defocus offset within the wavefront measurement range with or without the accommodation change of the eye over the accommodation range so that a better and more precise measurement of the eye refractive errors can be obtained.

It should be noted that the defocus offsetting device described in FIG. 5 can include a set of configured lenses to allow a shifting of the focal range along the return beam optical axis. The position and axial spacing of these lenses provides an offset that can actively remove or adjust the spherical refractive error component of the transmitted beam. This active focusing alters the divergence or convergence of the beam to "fit" or allow matching of the beam focusing properties in order to accentuate other aberration properties such as the appearance of the elliptically shaped beam pattern indicating an astigmatic condition. This "fitting process" does change the spherical power of such a beam with an exact knowledge of the amount of compensatory focal change. The first order linear focal shift introduced by the offsetting active lens(es) does(do) not alter the properties of the other inherent aberrations, it serves the basic purpose of highlighting and emphasizing the underlying higher order aberrations that are present. The sensitivity to detection of the existing higher order aberrations increase with more exact fitting location as the spherical refractive error component of the aberration is "matched" or "fitted" allowing better appreciation and detection of wavefront changes imposed by the lesser slope values which can be masked by large spherical wavefront slope values.

This can be visualized by considering the appearance of the globe of the earth which has a larger base spherical shape with myriad small slope changes caused by the local terrain changes with mountain ranges being a positive local slope change and valleys being a negative slope change. If one were to flatten out the large linear spherical component of the earth the remaining lesser slope changes would become increasingly apparent as well as the better definition of the non-spheroid general elliptical shape of the globe. This active defocus offsetting acts only on the linear spherical component of the collected returned beam.

It should be noted that although a positive plus negative lens combination with relative axial movement is used as the defocus offsetting element in FIG. 5, other focus variable optical element can be used, including liquid or solid focus variable lenses, voice coil or motor driven movable lens(es), liquid crystal lens(es), acousto-optic lens(es), deformable mirror(s) and diaphragm(s). The position of the defocus offsetting element does not need to be right in front of the wavefront sensor and can be anywhere along the optical path as long as it serves the function of offsetting the defocus of the wavefront. In fact, for a compact design the defocus offsetting element can be designed together with other optical element(s) inside the wavefront sensor 528. For example, it can be combined with the front focusing lens 504 of the sequential wavefront sensor 528. Such a real time sequential wavefront can be made with a small form factor and thus be integrated into a large number of optical imaging or measurement systems, such as an eye refractive surgical microscope. It should also be noted that although a sequential wavefront sensor 528 has been illustrated in FIG. 5, other types of wavefront sensors can also be used as long as it can provide wavefront measurement, including Hartmann-Shack, Talbot-Moire, Tscherning, Ray-tracing, phase diversity and interferometric wavefront sensors.

The electronic control and detection system 532 coordinates the activation of all active elements, including the defocus offsetting device 505, the focusing lens 582 of the near infrared imaging camera 584, the accommodation changing element 546 of the internal fixation/visual acuity projector 542 and others.

Figure 6:
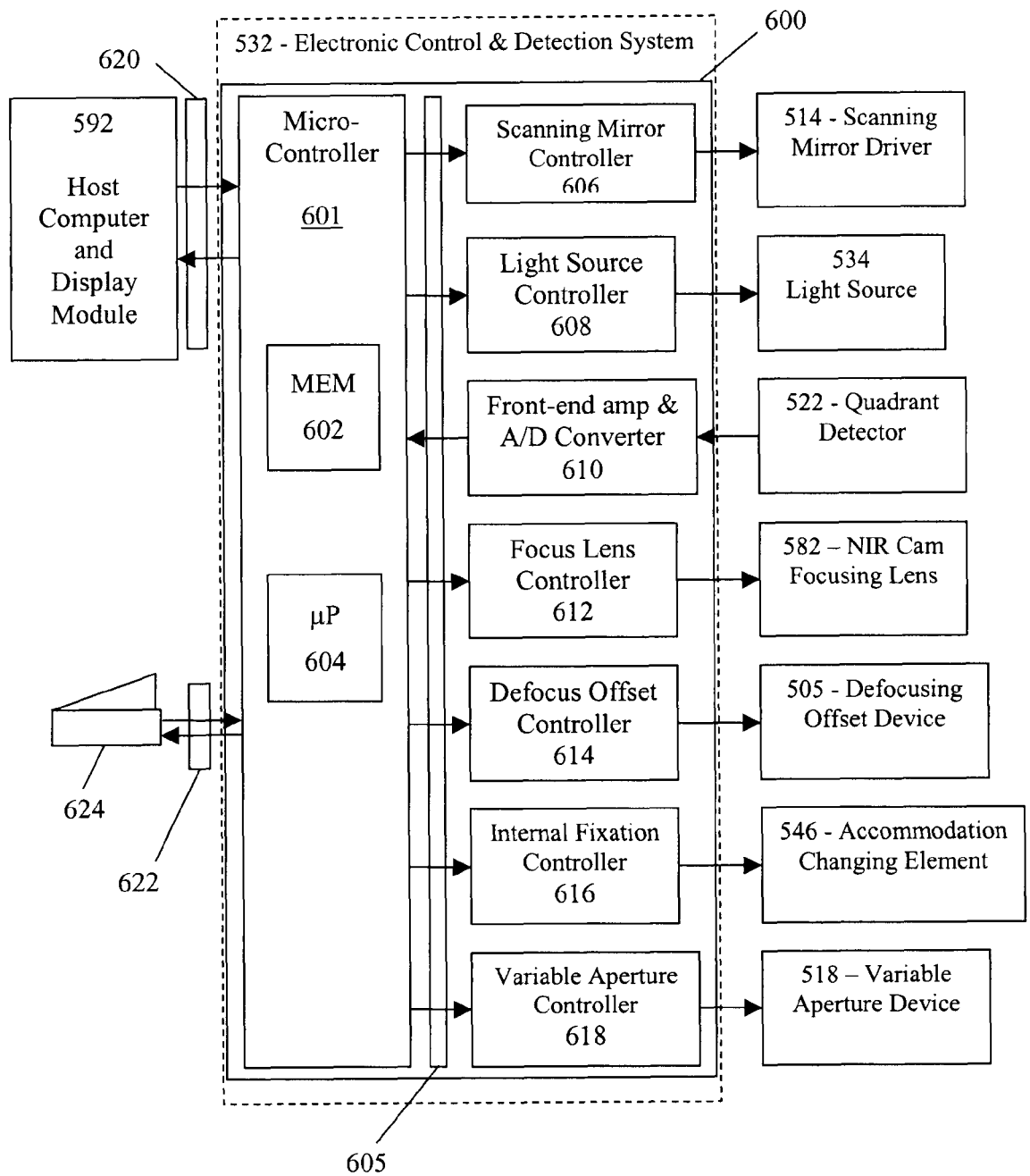
FIG. 6 shows a block diagram of a typical electronic control and detection system that is illustrated in FIG. 5.

FIG. 6 is a detailed block diagram of an example embodiment the electronic control and detection system 532. A printed circuit board (PCB) 600 includes a micro-controller 601 having a memory 602 for storing program code and data, and a processing unit 604 for executing the program code and processing the data. The microcontroller has an I/O interface (indicated by arrows) 605 coupled to various control modules 606 to 618. The control modules are interfaced with the various components of the deterministic dynamic wavefront sensing system depicted in FIG. 5 using standard techniques.

The PCB 600 also includes a host-side interface 620 for interfacing with the host computer and display module 592 and a user interface 622 for interfacing with a user interface device such as a foot pedal 624. The foot pedal can be configured to allow a surgeon to "zoom in" or "zoom out" by controlling the position of the defocusing mechanism.

The memory 602 is configured to store programs executed to perform the algorithms described below to control the deterministic dynamic wavefront sensing system depicted in FIG. 5. The various modules depicted in FIG. 6 may be implemented as discrete parts or integrated onto ASICs or other programmable devices.

The microcontroller 601 can send control signal to a scanning mirror controller connected 606 to a scanning mirror driver to drive the scanning mirror 514 and can send control signals to a light source controller 608 to turn the light source 534 on and off. Further, the microcontroller can receive signals from the quadrant detector 522 as shown in FIG. 5 through a front-end amplifier and an A/D converter 610. In addition, the microcontroller can also control the NIR camera focusing lens 582 through a focus lens controller 612. One key function of the microcontroller is to offset the defocus of the defocus offset device 505 through a defocus offset controller 614. More additional functions that the microcontroller can provide include changing the accommodation of the patient eye by controlling the accommodation changing element 546 through an internal fixation controller 616, and changing the subwavefront sampling aperture size of the variable aperture device 518 through a variable aperture controller 618. The function of the electronic control and detection sub-system can be provided by a dedicated micro-processor or a computer or other electronic processing means and therefore, the electronic control and detection system 532 shown in FIG. 5 should only be considered as an optional component but not as an absolutely needed item for the apparatus.

The display module 592 shown in FIG. 5 is included because it can be viewed directly by a refractive surgeon during a vision correction procedure to guide him/her in selecting the desired defocus offset and in optimizing the vision correction outcome. It should, however, be noted that the display module 592 in FIG. 5 should be interpreted broadly as a real time feedback means. In fact, for a vision correction surgical procedure under a surgical microscope, an approach to implement the display of the real time wavefront measurement is to incorporate a micro display inside the surgical microscope so that the wavefront measurement result can be overlaid onto the image of the patient's eye formed by the surgical microscope and presented to the refractive surgeon directly. In doing so, the surgeon does not need to move his/her head away from the binocular of the surgical microscope.

The wavefront can be sampled according to a sampling pattern while offsetting some lower order aberrations so that information on some particular higher order wavefront aberrations can be clearly highlighted or vice versa. For example, by dynamically offsetting defocus and compensating astigmatism, higher order aberration (HOA) content, such as coma, which is a very prevalent HOA that surgeons are becoming familiar with and have techniques to address surgically, can be highlighted and displayed in a format easily understandable by clinical practitioners.

In the present embodiment, the micro-controller 601 further executes a program stored, for example, in memory 602 to implement the steps described above with reference to FIG. 2. The user provides input and receives output through the attached host computer and display module 592. Alternatively, the user input can be directly provided to the microcontroller 601 through a connected user-input device and the output coupled to an output device.

In another embodiment, the micro-controller 601 would output the raw data to the host computer and display module 592 and the processing described above with reference to FIG. 2 would be performed by the host computer and display module 592.

The above described embodiments can be used in a variety of applications. For example, it can be used in a lensometer to measure and fine tune the refractive power of a lens including a spectacle lens, a contact lens, and/or an IOL. Although various embodiments that incorporate the teachings of the present invention have been shown and described in detail herein, those skilled in the art can readily devise many other varied embodiments that still incorporate these teachings.

What is claimed is:

1. An apparatus comprising: a wavefront sensor configured to capture raw wavefront aberration data values of an eye; a user-input device configured to allow an end user to select one of a plurality of predefined processes, as algorithms, filters and analyses, where a selected predefined process manipulates raw wavefront aberration data values to assess or alter the raw wavefront aberration data values and outputs resultant data in various forms; a non-transitory computer readable storage device holding one or more raw wavefront aberration data values, captured by the wavefront sensor a measurement device, and program code; a controller, coupled to the storage device and user-input device configured to execute the program code to assign one or more raw wavefront aberration data values a the user-selected process, algorithm that processes one or more of the variables to execute the user-selected process to assess or alter the one or more raw wavefront aberration data values and to output the resultant data.

2. The apparatus of claim 1 further comprising:
a display device coupled to the controller and configured to display resultant data output by the controller.

3. The apparatus of claim 1 where:
the raw wavefront aberration data values are spherical and cylindrical refractive error values.

4. The apparatus of claim 1 where:
the raw wavefront aberration data values are high-order aberration values.

5. The apparatus of claim 1 where:
the raw wavefront aberration data values are coma, trefoil and spherical aberration values.

6. The apparatus of claim 1 where:
the raw wavefront aberration data values are the measured spherical refractive error (u) and the measured cylindrical refractive error (v) of an aphakic eye, where the selected process manipulates the raw wavefront aberration data values to determine a resultant value of $w=0.07(u+0.5v)^2+1.27(u+0.5v)+1.22$, with w being the power of an intraocular lens (IOL) and where u, v, and w are output by the controller in the form of a table.

7. The apparatus of claim 1 where:
the selected process manipulates a polynomial of a variable and a raw wavefront aberration datum value is assigned to the variable.

8. An apparatus comprising:
a sub-wavefront focusing lens configured to focus a sub-wavefront, being an incident portion of a wavefront generated by a light source, to an image spot located on a focal plane;
a sequential wavefront scanning device configured to sequentially project different portions of an incident wavefront on the sub-wavefront focusing lens;
a variable aperture configured to control the size of the sub-wavefront;
a position sensing device, located substantially at the focal plane of the sub-wavefront focusing lens, configured to indicate the location of the image spot on the focal plane;
a controllable wavefront offsetting element positioned to intercept the portion of the wavefront before it is incident on the wavefront sensor;
a user-input device;
a non-transitory computer readable storage device holding one or more data values captured by a measurement device and a program;
and
a controller, coupled to the controllable wavefront offsetting element, the user input device and the storage device, configured to control the controllable wavefront offsetting element to offset selected wavefront aberration components of the wavefront in order to measure one or more remaining aberration components of the portion of wavefront, to execute the program to assign one or more remaining wavefront aberration components to one or more corresponding variables, to receive a user-selected algorithm that processes one or more of the variables to assess or alter the one or more variables to provide a resultant value and to output the resultant value.

9. The apparatus of claim 8 further comprising:
a display device; and
with the controller further configured to display the one or more variables and assigned data values.

10. The apparatus of claim 8 where:
the remaining aberration components are spherical and cylindrical refractive error values.

11. The apparatus of claim 8 where:
the remaining aberration components are high-order aberration values.

12. The apparatus of claim 11 where:
the remaining aberration components are coma, trefoil and spherical aberration values.

13. An apparatus comprising:
a sub-wavefront focusing lens configured to focus a sub-wavefront, being an incident portion of a wavefront generated by a light source, to an image spot located on a focal plane;
a sequential wavefront scanning device configured to sequentially project different portions of an incident wavefront on the sub-wavefront focusing lens;
a variable aperture configured to control the size of the sub-wavefront;
a position sensing device, located substantially at the focal plane of the sub-wavefront focusing lens, configured to indicate the location of the image spot on the focal plane;
a user-input device;
a non-transitory computer readable storage device holding one or more data values, captured by a measurement device, and a program;
and
a controller, coupled to the user input device and the storage device, configured to execute the program to assign one or more data values to one or more corresponding variables, to execute a user-selected process that processes one or more of the variables to assess or alter the one or more variables to provide a resultant value and to output the resultant value in a specified format.

14. The apparatus of claim 13 further comprising:
a display device; and
with the controller further configured to display the one or more variables and assigned data values.

* * * * *

UNITED STATES PATENT AND TRADEMARK OFFICE
CERTIFICATE OF CORRECTION

PATENT NO.        : 8,002,410 B2                                Page 1 of 1
APPLICATION NO.   : 12/643945
DATED             : August 23, 2011
INVENTOR(S)       : Shea It is certified that error appears in the above-identified patent and that said Letters Patent is hereby corrected as shown below:

CLAIM 1 TO READ AS FOLLOWS:

1. An apparatus comprising:
a wavefront sensor configured to capture raw wavefront aberration data values of an eye;
a user-input device configured to allow an end user to select one of a plurality of predefined processes, as algorithms, filters and analyses, where a selected predefined process manipulates raw wavefront aberration data values to assess or alter the raw wavefront aberration data values and outputs resultant data in various forms;
a non-transitory computer readable storage device holding one or more raw wavefront aberration data values, captured by the wavefront sensor, and program code;
a controller, coupled to the storage device and user-input device, configured to execute the program code to assign one or more raw wavefront aberration data values to the user-selected process, to execute the user-selected process to assess or alter the one or more raw wavefront aberration data values and to output the resultant data.

Signed and Sealed this
Twenty-ninth Day of November, 2011

David J. Kappos
*Director of the United States Patent and Trademark Office*

UNITED STATES PATENT AND TRADEMARK OFFICE
CERTIFICATE OF CORRECTION

PATENT NO. : 8,002,410 B2  
APPLICATION NO. : 12/643945  
DATED : August 23, 2011  
INVENTOR(S) : Shea Page 1 of 1

It is certified that error appears in the above-identified patent and that said Letters Patent is hereby corrected as shown below:

Column 8, lines 13-29, CLAIM 1 SHOULD READ AS FOLLOWS:

1. An apparatus comprising:
a wavefront sensor configured to capture raw wavefront aberration data values of an eye;
a user-input device configured to allow an end user to select one of a plurality of predefined processes, as algorithms, filters and analyses, where a selected predefined process manipulates raw wavefront aberration data values to assess or alter the raw wavefront aberration data values and outputs resultant data in various forms;
a non-transitory computer readable storage device holding one or more raw wavefront aberration data values, captured by the wavefront sensor, and program code;
a controller, coupled to the storage device and user-input device, configured to execute the program code to assign one or more raw wavefront aberration data values to the user-selected process, to execute the user-selected process to assess or alter the one or more raw wavefront aberration data values and to output the resultant data.

This certificate supersedes the Certificate of Correction issued November 29, 2011.

Signed and Sealed this  
Third Day of January, 2012

David J. Kappos  
*Director of the United States Patent and Trademark Office*